Feb. 22, 1949. G. C. SPARRE Plant Pat. 826
CHRYSANTHEMUM PLANT
Filed June 19, 1947
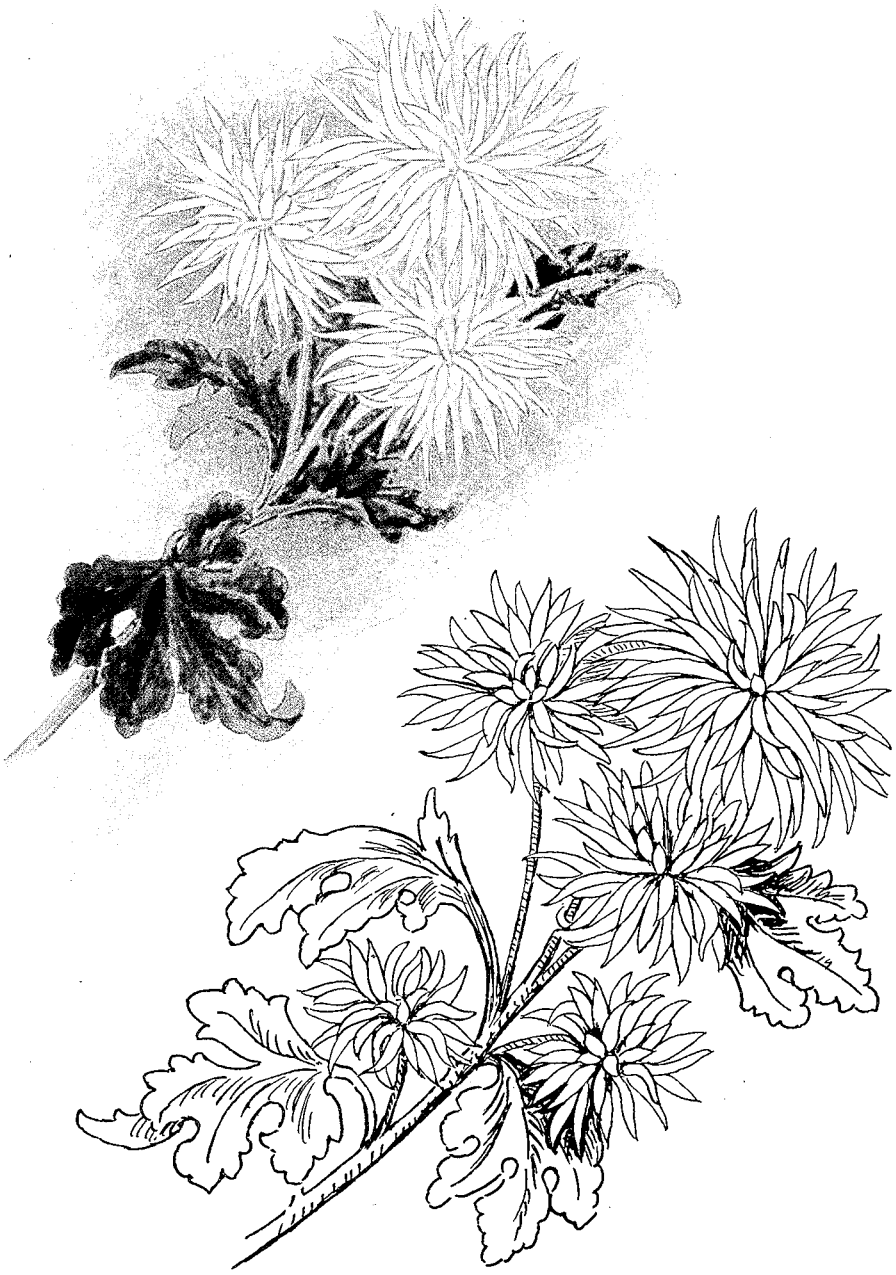
WITNESS
Addison E. Avery
INVENTOR
Gustav C. Sparre
by: John Harrow Leonard
his ATTY.

Patented Feb. 22, 1949

Plant Pat. 826

UNITED STATES PATENT OFFICE

826

CHRYSANTHEMUM PLANT

Gustav C. Sparre, Clarkson, Ontario, Canada, assignor to John J. Grullemans, Mentor, Ohio Application June 19, 1947, Serial No. 755,682

1 Claim. (Cl. 47—60)

This invention relates to a new and distinct variety of chrysanthemum plant.

The drawing shows in one view, in color, the terminal of one of the main stalks with the terminal inflorescence and leaves and a similar view in black and white indicating the structure in more detail.

The new variety was produced by me by crossing the chrysanthemum plant known as Mrs. Dunington Grubb, as the seed parent, with the chrysanthemum plant Snowbird, as the pollen parent, both the seed parent and the pollen parent being crosses made by me between the *Chrysanthemum indicum* and the Korean strain. The new variety was first produced by me in my gardens at Clarkson, Ontario, Canada, and was first asexually reproduced by me by root cuttings. Subsequently, it was asexually reproduced by root cuttings in the test fields of The Wayside Gardens Company, of Mentor, Ohio. The original plant is still growing in my gardens at Clarkson, Ontario.

The plant has shallow, fibrous massed roots of medium size and of the usual spread, being about equal to the spread of the upper portion of the plant. The roots have a good resistance to disease, wetness, drought and winter weather, having withstood, unprotected, winter weather with temperatures of as low as 12° to 15° (F.) below zero.

The exposed plant is herbaceous, upright and medium compact, having an average height of 18 to 20 inches the first year and about 36 inches in the second or third year. Its spread is about 18 to 24 inches. It is generally oval-shaped and a vigorous grower. The resistance of the exposed plant to disease, drought and wetness and lower temperature, both protected and unprotected, is good. It prefers moderate sun and does well in any good well-drained garden loam under the usual growing conditions suitable for chrysanthemum plants.

The main stalks are upright, herbaceous and much branched. They are relatively stiff with a tendency toward brittleness and are generally adequate to support the foliage and bloom well. They are generally dark green, comparable to Maerz and Paul Plate 22–B–1, with a tendency toward brownish green, comparable to Maerz and Paul Plate 15–C–7, near the bottom. The color is quite uniform. The main stalks average from 30 to 36 inches in length, are of smooth surface texture, and grow divergently from the roots. The branches are whorled, of dark green color and have a hirsute surface texture.

The foliage is loose, in whorled arrangement, and abundant. The leaves are of a dull green, comparable to Maerz and Paul Plate 24–L–2, on top and a lighter green, comparable to Maerz and Paul Plate 22–B–1, on the under surface. The color is generally uniform and the leaves are of average shape and size of medium thickness. They are of hirsute texture on both the upper and lower faces and their peristency on the plant is excellent. The petioles or leaf stems are dull green in color and the surface texture is smooth. They are of medium strength.

The plant blooms well throughout the entire United States but for best blooming prefers the sun with a southern exposure and a reasonably moist, fairly cool location. It prefers a moist but well drained neutral loam soil and both the quality and quantity of the blooms is best when it has at least a half day's sun, cool weather and fairly moist soil. The color is not affected appreciably by changes in these conditions. The number of blooms is about the same under all normal growing conditions but none is produced in deep shade. Both heat and shade tend to reduce the size of the blooms but do not affect the color. The plant blooms throughout September but sometimes starts in late August. It blooms continuously throughout the blooming period and the period is lengthened if the old flowers are removed.

The buds are of the usual size and globular form and are borne upright. When the sepals first divide the buds are of a deep yellow ochre color which changes to a lighter yellow ochre when the petals begin to unfurl and becomes a soft corn yellow when the buds are half blown. When full blown, the blossoms are a yellow ranging from Maerz and Paul Plate 9–L–3 throughout 9–L–6. The blooms average in size from three to four inches in diameter and are borne thirty to fifty on a plant in heads or clusters of three or four to a stem. They are very persistent and long lasting both when cut and uncut. The petals are of a color which I would describe as a deep yellow ochre at the beginning of the blooming and which changes gradually to an apricot buff and then to a soft corn yellow as the blooming period of each flower progresses. This color is uniform from the center of the flower outwardly and at the base and reverse of the petals. The general tonality from a distance changes from a deep yellow ochre to an apricot buff and then to a soft corn yellow as the blooming period progresses.

The petals are of a smooth texture and of smooth waxy appearance, both inside and outside. They are generally lanceolate and very narrow, being sharply pointed at both ends and relatively thin. They are arranged similar to the petals of a cactus dahlia but are not imbricated. The flower is similar to the flower of a cactus dahlia, being shaggy, fully double, globular but graceful in appearance. There are no petaloids in the center. The bloom has a faint chrysanthemum fragrance.

The stamens are composite and the fruit is of the usual form but insignificant and sparse.

The flowers are produced in open clusters which permits a fine showing of their details.

I claim:

The new variety of chrysanthemum plant herein shown and described characterized in that its flowers are produced in open clusters, are fully double, are shaped like a cactus dahlia and are large yet very graceful in appearance and have an exceptional color, beginning with a deep yellow ochre at the start of the blooming season and changing during the blooming season to an apricot buff and then to a soft corn yellow, and the plant is exceedingly vigorous, of exceptional resistance to disease and of good resistance to drought, and its roots have the ability to withstand severe winters, both protected and unprotected.

GUSTAV C. SPARRE.

No references cited.